US006981953B1

(12) United States Patent
Ko

(10) Patent No.: US 6,981,953 B1
(45) Date of Patent: Jan. 3, 2006

(54) DUAL-FUNCTIONAL MASSAGE BAR USED IN BATH

(76) Inventor: Fu-Chung Ko, P.O. Box 697, Fongyuan City, Taichung County (TW) 420

( * ) Notice: Subject to any disclaimer, the term of this patent is extended or adjusted under 35 U.S.C. 154(b) by 0 days.

(21) Appl. No.: 10/983,602

(22) Filed: Nov. 9, 2004

(51) Int. Cl.
*A61F 11/00* (2006.01)

(52) U.S. Cl. ........................... 601/46; 601/72; 601/138

(58) Field of Classification Search .................. 601/72, 601/46, 47, 137, 138, 80; 482/69, 70, 124
See application file for complete search history.

(56) References Cited

U.S. PATENT DOCUMENTS

| | | | | |
|---|---|---|---|---|
| 5,582,581 | A * | 12/1996 | Horton | 601/70 |
| 5,637,065 | A * | 6/1997 | Chang | 482/114 |
| 6,485,444 | B1 * | 11/2002 | Gershov | 601/138 |
| 6,645,128 | B1 * | 11/2003 | Hur | 482/124 |
| 6,802,819 | B1 * | 10/2004 | Liao | 601/72 |
| 2002/0156402 | A1 * | 10/2002 | Woog et al. | 601/46 |

* cited by examiner

*Primary Examiner*—Michael A. Brown

(57) ABSTRACT

A dual-functional massage bar used in bath includes a main body which is combined by a pair of corresponding halves having a plurality of balls disposed spaced apart on one side, a piece of first Velcro attached to the other side opposite to the balls for engaging a piece of sponge which has a piece of second Velcro on underside engaged with the piece of the first Velcro, an externally threaded tubular adapter on the rear end of the main body in which is a motor and a vibrator, a tube having internal threads screwed onto the tubular adapter with a pair sealing rings engaged thereinbetween, a pair of batteries disposed into the tube and the adapter and biased by a spring and three switch buttons spacedly disposed on the front side of the main body and protected by a piece of thin membrane. The piece of sponge may be replaced by a brush and/or a piece of cloth.

6 Claims, 8 Drawing Sheets

DUAL-FUNCTIONAL MASSAGE BAR USED IN BATH

BACKGROUND OF THE INVENTION

The present invention relates to massage apparatus, and more particularly to a dual-functional massage bar which has massage and cleansing functions and a waterproof body so as to capable to use in the bath.

The conventional vibrated massage bars are in varied types and welcome by the population to massage their bodies for activating their muscles and relieving their exhaustions. But these massage bars are only useful on massage and can not be used to a bathe due to the lacking of waterproof. So that the people have to buy an expensive massage bathe and to utilize the bubbles and water flow to massage their bodies.

People are used to utilize a brush, a piece of sponge and/or a towel dipping some soap to wash their body. However, these articles have no any massage function.

Nowadays, there is no any apparatus in the market that can be utilized to simultaneously massage and clean the body in the bath. So either a massage bar or a cleansing article only achieves their single purposes.

SUMMARY OF THE PRESENT INVENTION

The present invention has a main object to provide a dual-functional massage bar used in bath which is utilized in massage and cleansing the body of a bather to activate his muscles and to simultaneously refresh his exhaustion.

Another object of the present invention is to provide a dual-functional massage bar used in bath which is attachable to a sponge, a brush and or a piece of cloth for the cleansing purpose.

Still another object of the present invention is to provide a dual-functional massage bar used in bath in which the handle is capable of increasing the length to facilitate the user to massage and/or to clean his back.

Further object of the present invention is to provide a dual-functional massage bar used in bath which is of waterproof and can be buoyed up on the surface of the water in a bath.

Accordingly, the dual-functional massage bar used in bath of the present invention comprises a hollow interior main body composed of two corresponding halves having an externally thread adapter including an opening, a massage surface on a first half which includes a plurality of spacedly arranged balls, a piece of Velcro (hooks & hoops) on the second half opposite to the massage surface for attaching a sponge, a brush and/or a cloth thereon. The sponge has a Velcro (hooks & hoops) in the bottom engageable with the Velcro (hooks & hoops) on the main body, two pieces of batteries inserted both into the opening of the adapter and an internally threaded tube which is then connected to the adapter with a pair sealing rings engaged therebetween for supporting the electric current dual-functional massage bar is of waterproof, it is capable of used in the bath.

The present invention will become more fully understood by reference to the following detailed description thereof when read in conjunction with the attached drawings.

DETAILED DESCRIPTION OF THE PREFERRED EMBODIMENT

Figure 1:
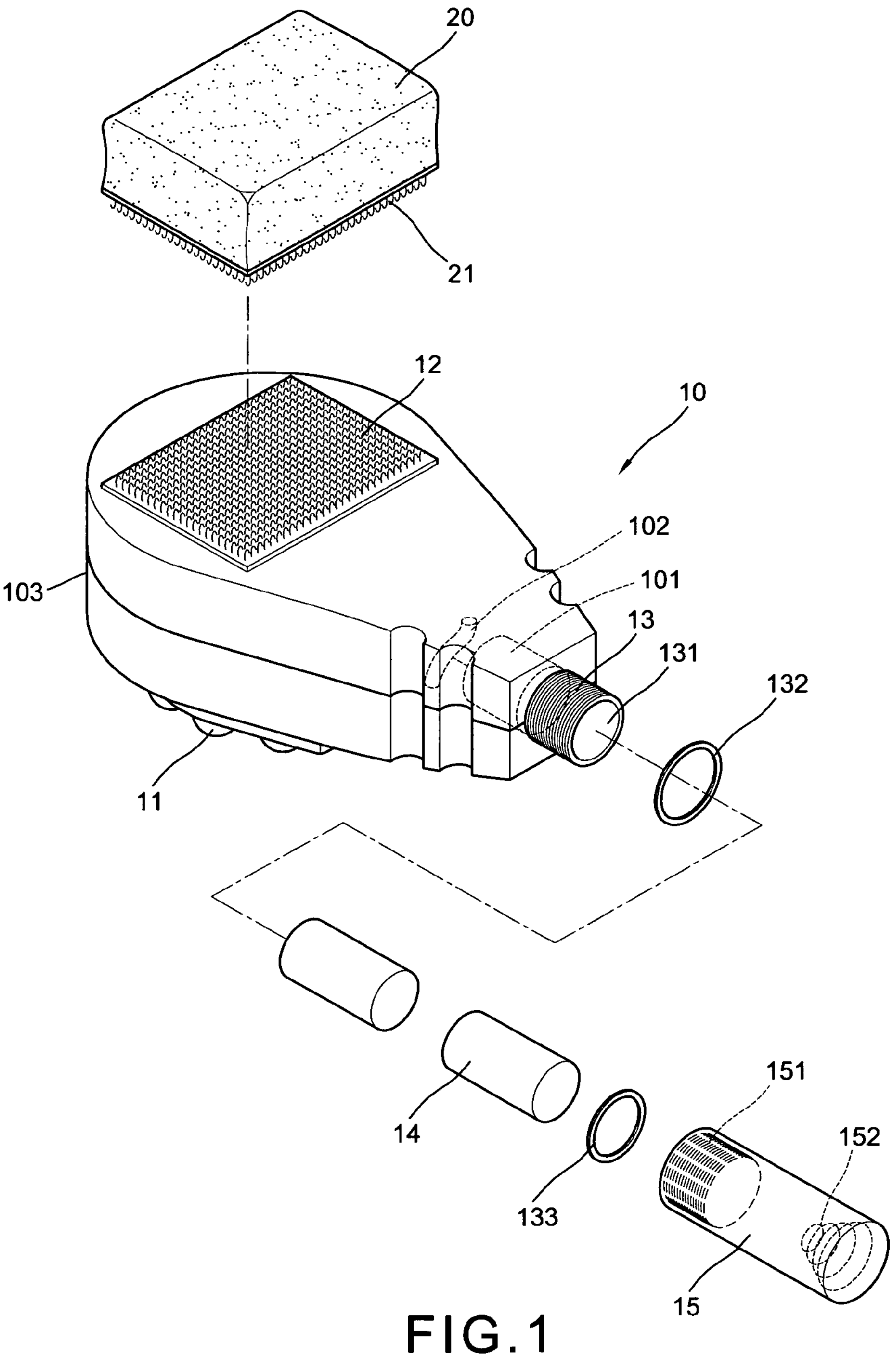
FIG. 1 is an exploded perspective view of the preferred embodiment of a dual-functional massage bar according to the present invention.
Figure 2:
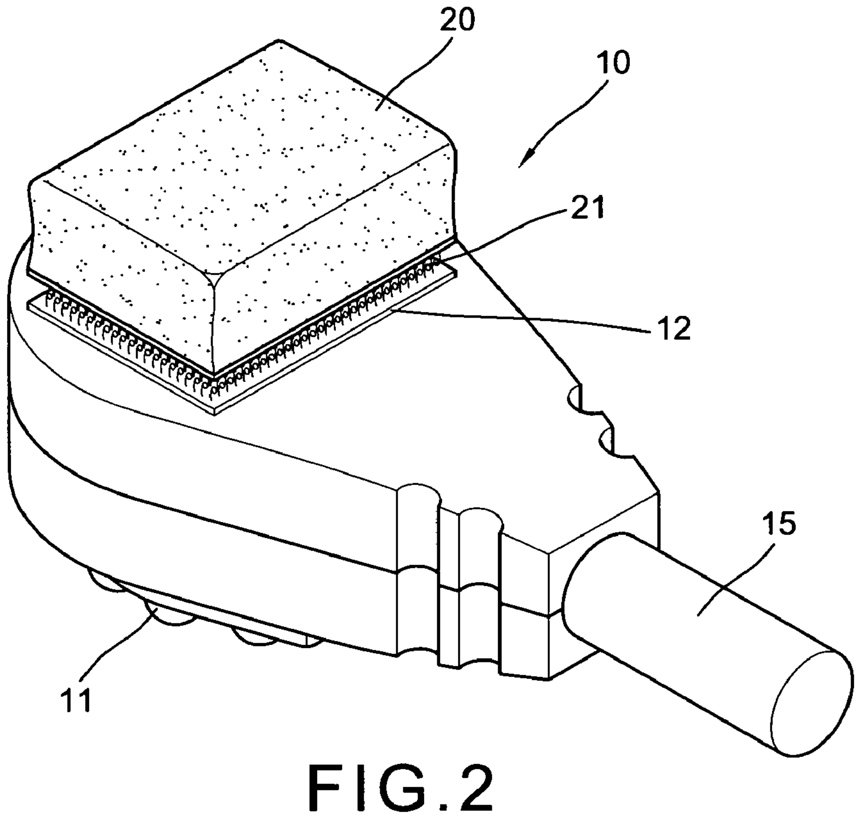
FIG. 2 is a perspective view to show the assembly of FIG. 1 looking from rearside.
Figure 3:
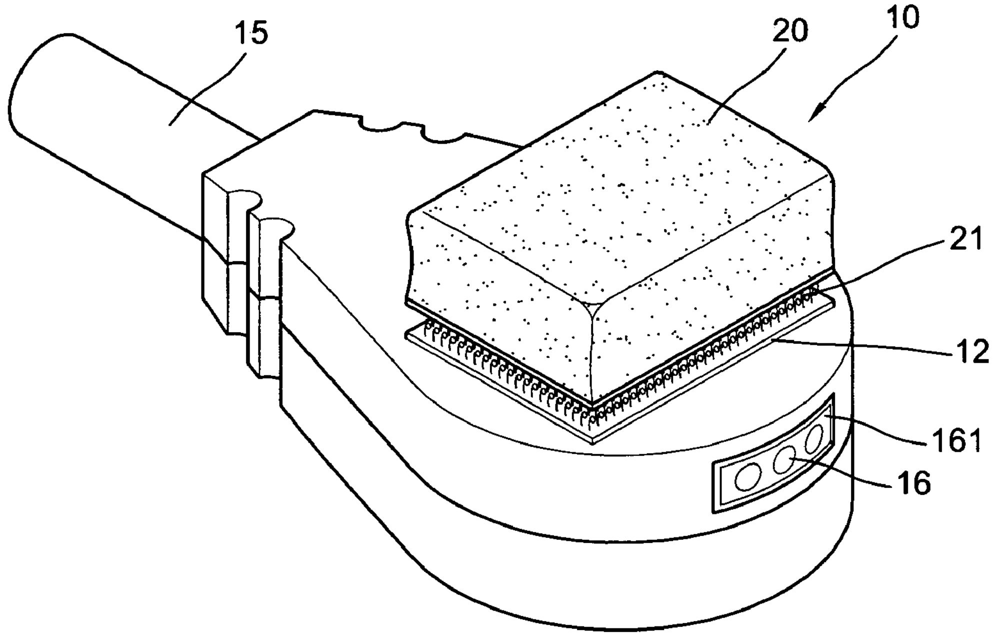
FIG. 3 is a perspective view to show the assembly of FIG. 1 looking from foreside.
Figure 4:
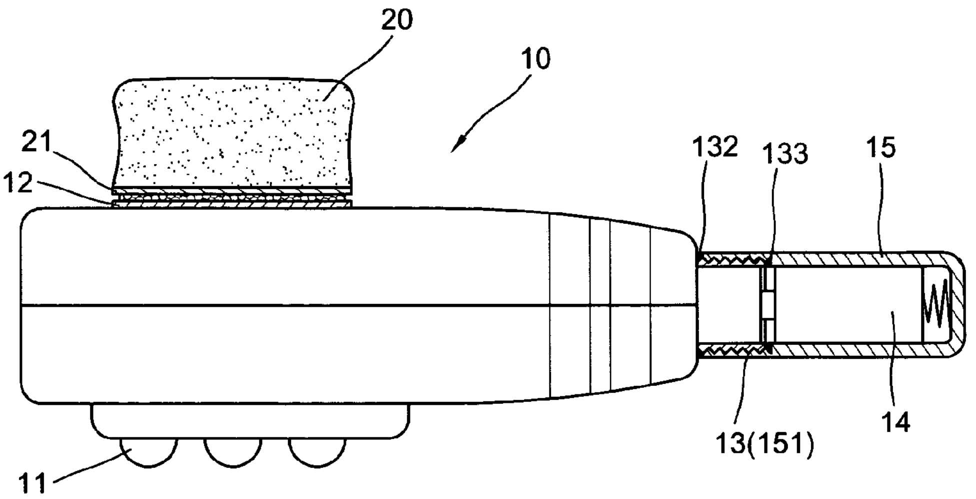
FIG. 4 is a side view of FIG. 2.
Figure 5:
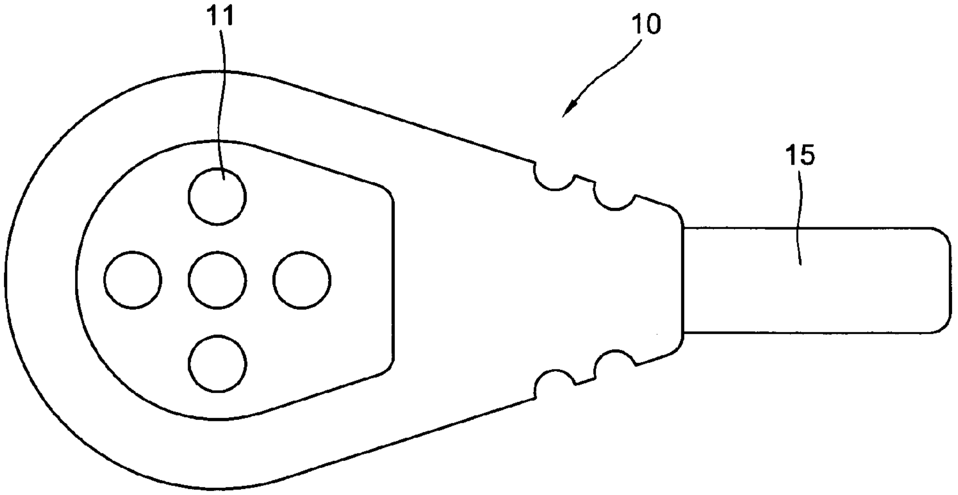
FIG. 5 is an underside view of FIG. 2.

With reference to the drawings and initiated from FIGS. 1 to 5, the dual-functional massage bar of the present invention comprises a hollow interior main body 10 which is composed of a pair of corresponding halves 11 and 12, a plurality of balls 11 disposed spaced apart on an underside, a piece of first Velcro 12 (hooks & hoops) on the top and an externally threaded tubular adapter 13 connected to the rear end communicating to the inside of the main body 10 including an opening 131 in free end for engaging with a tube 15 which has threads 151 on inner periphery engaged with the threads of the adapter 13 with a pair of sealing rings 132 and 133 engaged therebetween. The tube 15 has a sealed bottom and is provided to dispose a pair of batteries 14 which are biased by a spring 152 and inserted into the adapter 13 for supplying electricity to a motor 101 and a vibrator 102 in the main body 10. The coupling seam 103 between the two halves 11 and 12 is dealt with the waterproof process.

Three buttons 16 dispose spaced apart on the front side of the main body 10 and sealed by a thin membrane 161 for switching on/off the electricity. Note that the piece of sponge 20 may be replaced with a brush and/or a piece of the cloth.

In operation, switch on the electricity, the vibrator 102 begins to act to massage the body or to clean the body of the user in the bath. Due to that the massage bar is of complete waterproof and has adequate air therein, it is capable of buoyed on the surface of the water, especially used in a Japanese type bath or in a hot spring pool where the people are usually crowded. Once the user is unintentionally dropped the massage bar into the water, it will be automatically buoyed on the surface of the water so it is impossible to be lost. This massage bar can be also attached to a side of a bath to get the water molecules active and more oxidized by vibration that benefits to the skin cleansing.

Figure 6:
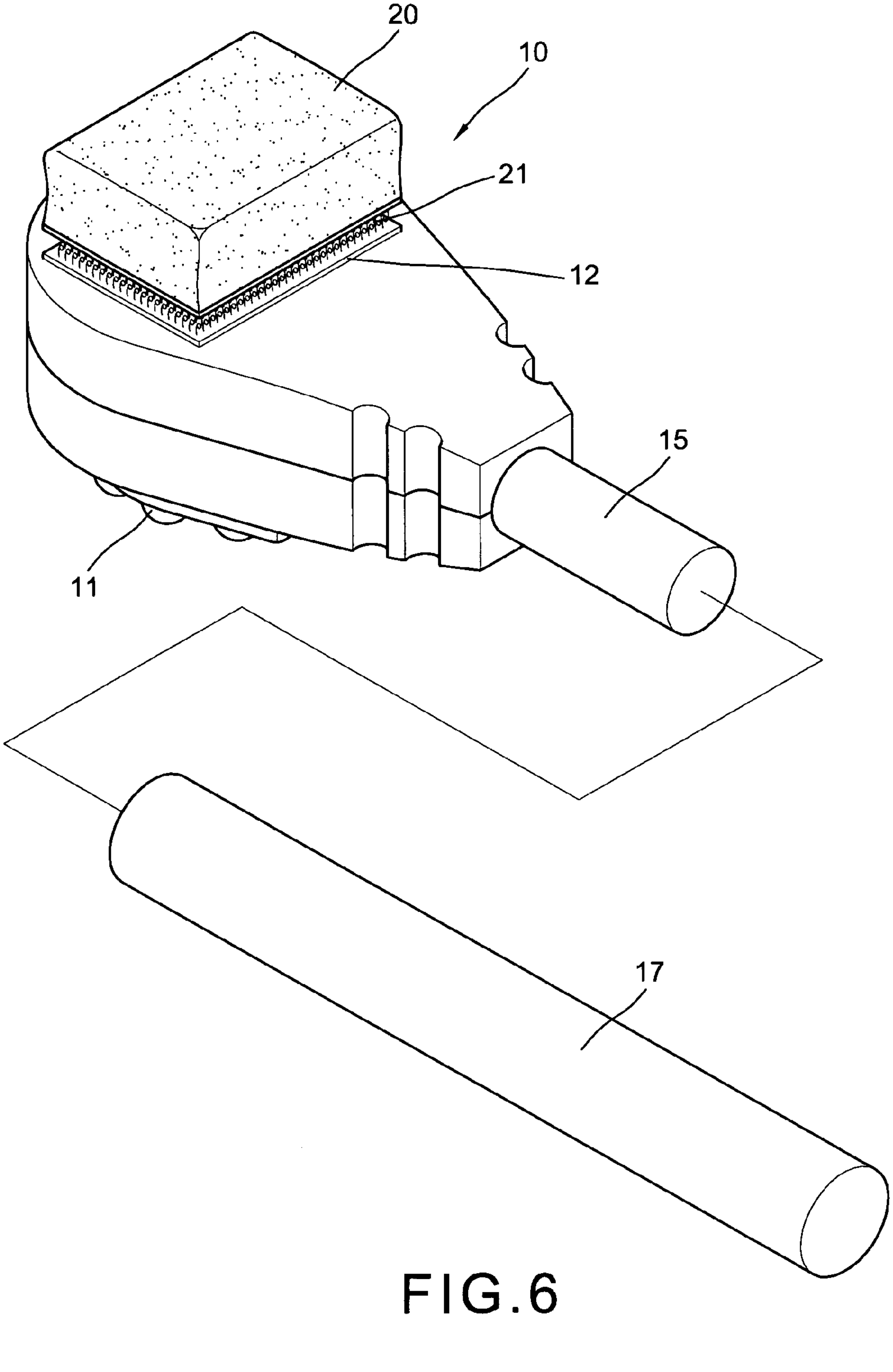
FIG. 6 is a perspective view to show an elongate tubular handle may connect to the tube.
Figure 7:
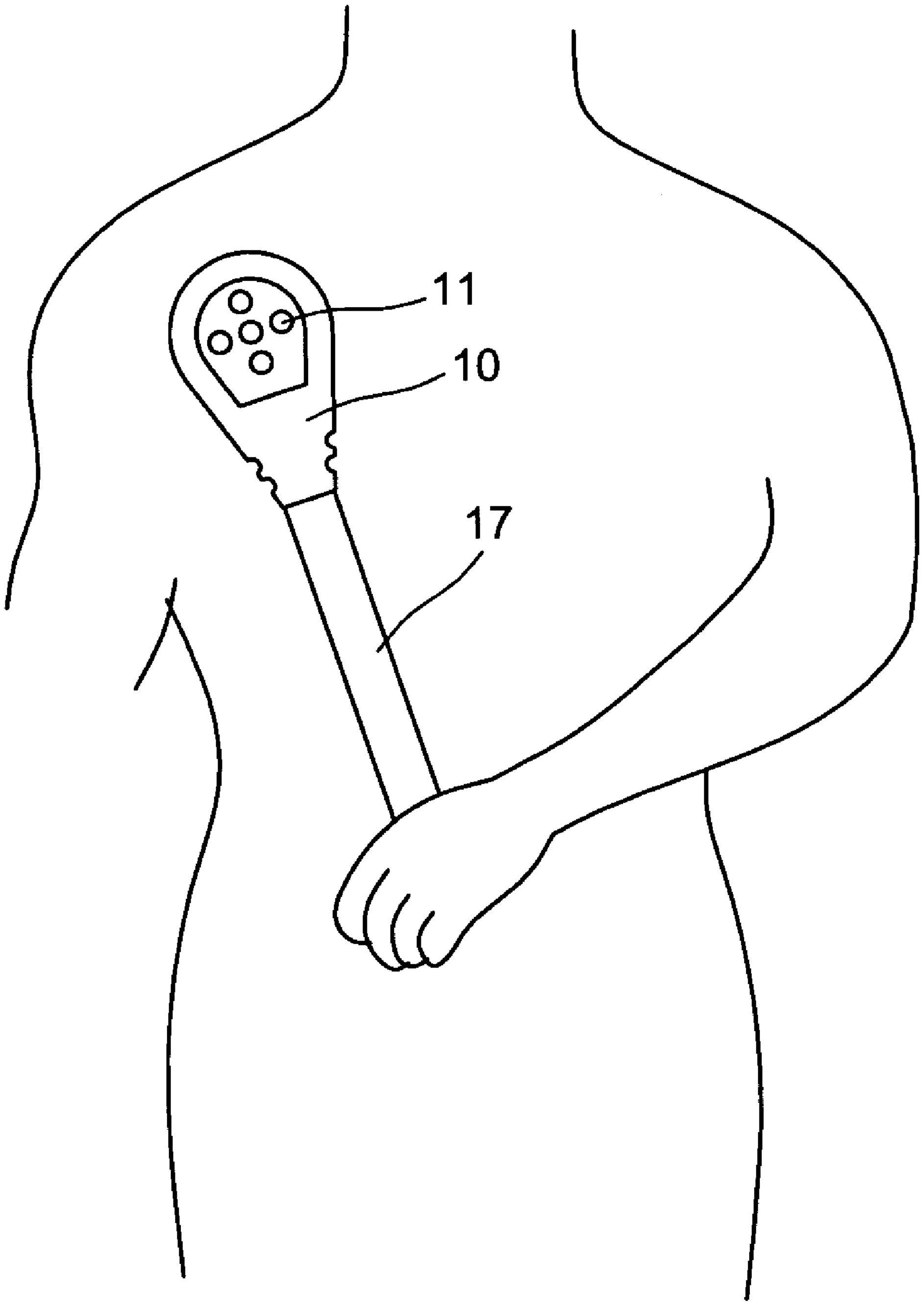
FIG. 7 is a plane view indicating that the dual-functional bar is operated by an user to clean his back.

Referring to FIGS. 6 and 7, a long tube 17 may be sleeved onto the tube 15 which has an outer diameter equal to the inner diameter of the long tube 17 for the elongation of the handle to facilitate the users to wash or massage their backs.

Figure 8:
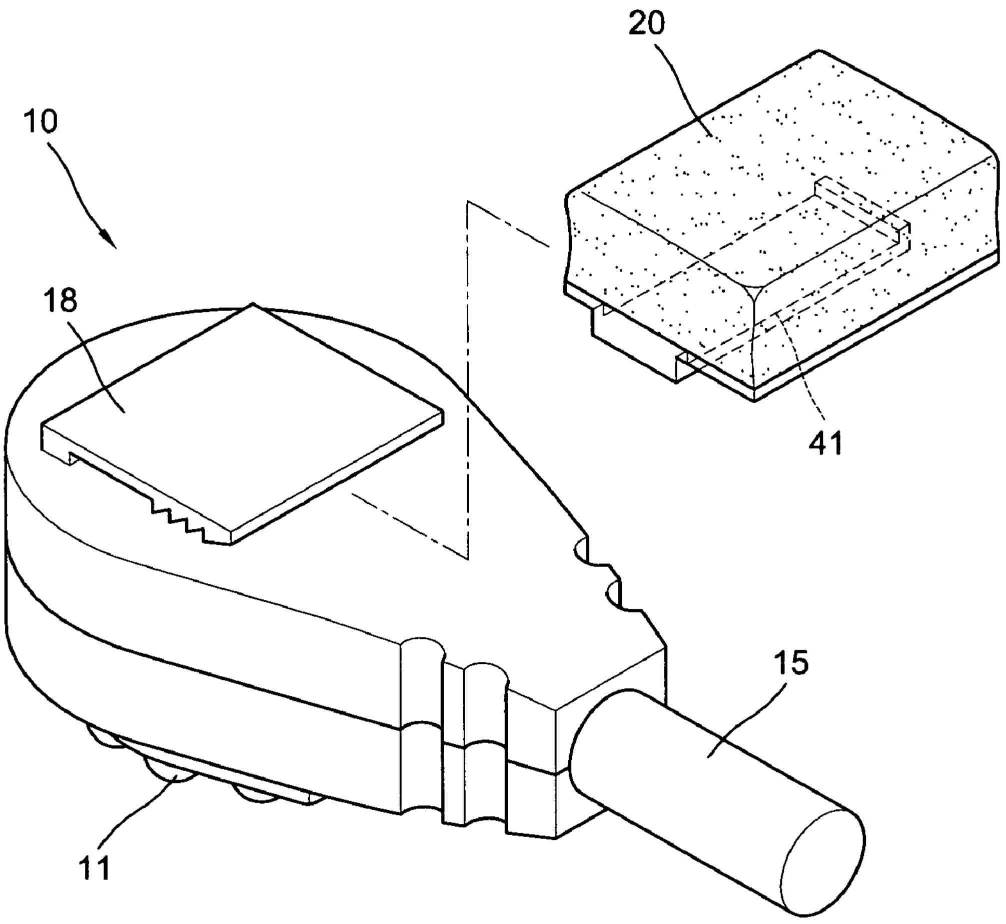
FIG. 8 is an exploded perspective view to show that the piece of Velcro (hooks & hoops) is replaced with a L-shaped clamping board and a coupling strip disposed on the underside of the sponge.
Figure 9:
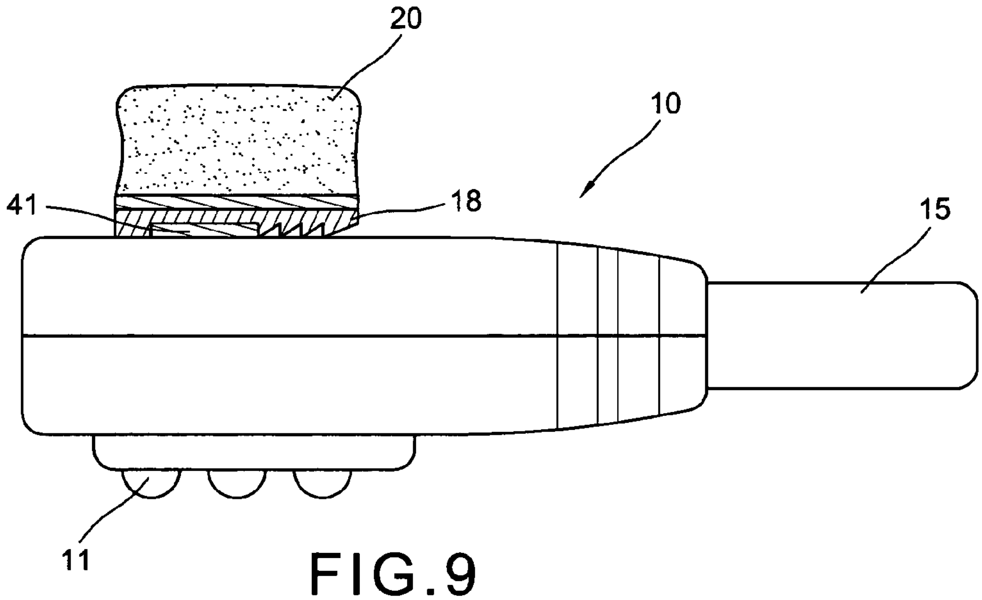
FIG. 9 is a side view to show that the strip of the sponge is engaged with the L-shaped clamping board.

Referring to FIGS. 8 and 9, the piece of Velcro (hooks & hoops) 12 on the main body 10 may be replaced with a L-shaped clamping plate 18. Meanwhile the piece of Velcro 21 under the piece of sponge 20 may be replaced with a strip 41 which is engageable with the clamping plate 18. This replacement does not affect the above described original functions of the present invention.

Figure 10:
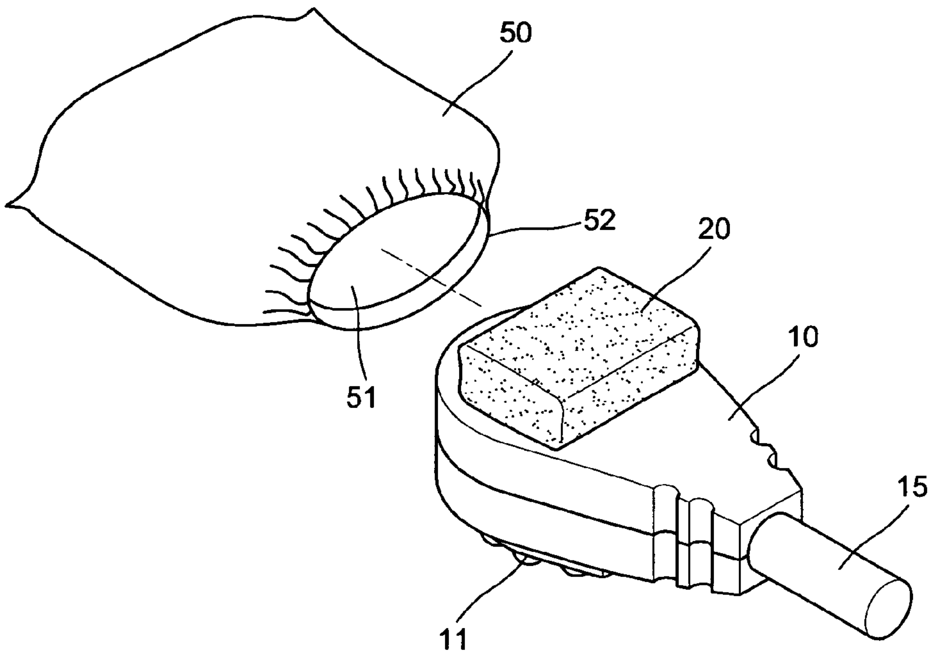
FIG. 10 is an exploded perspective view to show that a cloth bag is able to wrap the dual-functional massage bar.

Referring to FIG. 10, a cloth bag 50 may wrap the main body 10 without caring whether the piece of sponge 20 is existed. The bag 50 has an elastic band 52 on the opening 51 that restraints onto the rear end of the main body 10. This alternate arrangement also does not affect the above discussed functions of the present invention.

Figure 11:
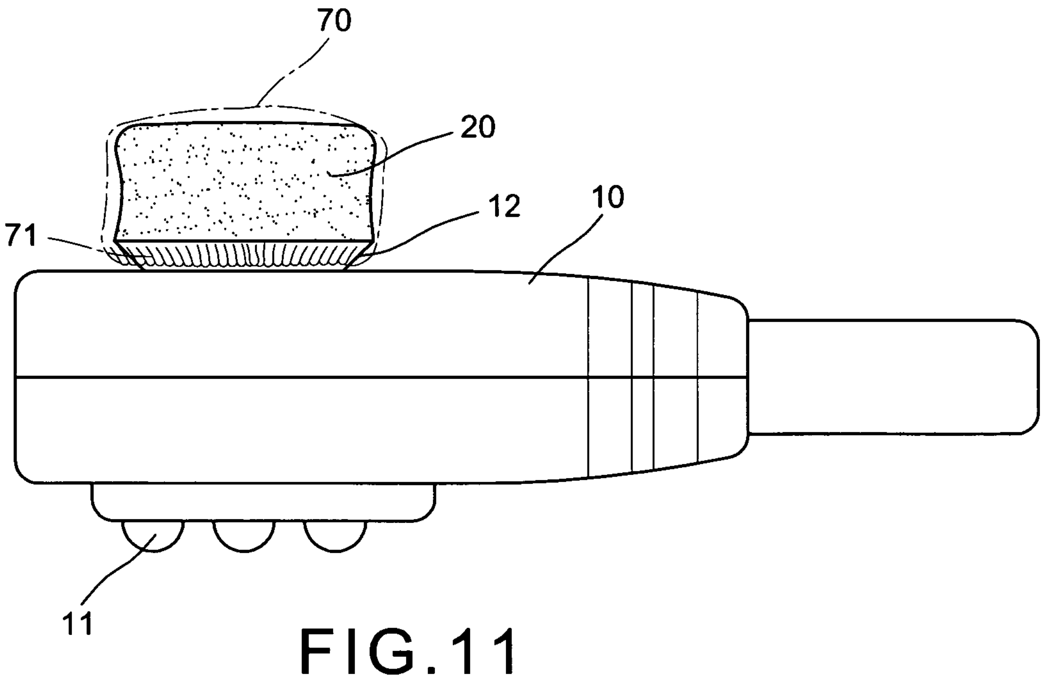
FIG. 11 is a side view to show that an elastic band secured to the underside of the sponge to replace the strip.

Referring to FIG. 11, a rectangular cloth bag 70 may wrap onto the piece of sponge 20 for protecting the piece of sponge 20. The rectangular cloth bag 70 has an elastic band 71 on lower opening to restraint the bottom of the piece of sponge 20. The way of operating the dual-functional massage bar is unchanged.

Except the above discussed functions, the dual-functional massage bar is useful to the medical recovery treatment.

Note that the specification relating to the above embodiment should be construed as an exemplary rather than as a limitative of the present invention, with many variations and modifications being readily attainable by a person of average skill in the art without departing from the spirit or scope thereof as defined by the appended claims and their legal equivalents.

I claim:

1. A dual-functional massage bar used in bath comprising:

a main body which is combined with a pair of corresponding halves having a plurality of balls disposed spaced apart on one side and a piece of first hooks & hoops attached to other side thereof opposite to said balls, a tubular adapter having threads on an outer periphery on rear end thereof communicating to inside of the main body in which is a motor and a vibrator;

a piece of sponge having a piece of second hooks & hoops on underside engaging the piece of first hooks & hoops on the main body;

a tube which has threads on an inner periphery engaged with the threads on an outer periphery of said adapter with a pair of sealing rings engaged thereinbetween;

a pair of batteries disposed in said tube and said adapter and biased by a spring;

Three switch buttons spacedly disposed on front side of said main body and protected by a thin membrane.

2. The dual-functional massage bar as recited in claim 1, wherein said piece of sponge may be replaced with a brush and/or a piece of cloth.

3. The dual-functional massage bar as recited in claim 1, further has a long tube attachable onto the tube of said main body.

4. The dual-functional massage bar as recited in claim 1, wherein said first hooks & hoops is replaced with a L-shaped clamping plate and said second hooks & hoops on underside of said piece of sponge is replaced by a strap engageable within said clamping plate.

5. The dual-functional massage bar as recited in claim 1, further has a cloth bag wrapped on said main body and includes an elastic band on an opening restrainted to rear end of said main body.

6. The dual-functional massage bar as recited in claim 1, further has a rectangular cloth bag wraps on said piece of sponge including an elastic band on an opening restrainted the underside of said piece of sponge.

* * * * *